US006712803B1

(12) United States Patent
Paritsky

(10) Patent No.: US 6,712,803 B1
(45) Date of Patent: Mar. 30, 2004

(54) DRUG DISPENSING SYSTEM

(76) Inventor: Howard Paritsky, 34 Farm to Market Rd., Brewster, NY (US) 10509

( * ) Notice: Subject to any disclaimer, the term of this patent is extended or adjusted under 35 U.S.C. 154(b) by 0 days.

(21) Appl. No.: 09/371,174

(22) Filed: Aug. 11, 1999

(51) Int. Cl.[7] .............................................. A61M 31/00
(52) U.S. Cl. .......................... 604/500; 604/73; 604/37; 604/212; 604/217; 604/246; 604/94; 128/200.22
(58) Field of Search ................................ 604/48, 73, 74, 604/37, 54, 207, 217, 212, 246, 251, 911, 131, 500; 128/200.22, 898, 260.14; 222/1; 239/327

(56) References Cited

U.S. PATENT DOCUMENTS

| | | | | |
|---|---|---|---|---|
| 4,579,858 A | * | 4/1986 | Ferno et al. | 131/270 |
| 5,116,311 A | * | 5/1992 | Lofstedt | 604/516 |
| 5,362,496 A | * | 11/1994 | Baker et al. | 424/434 |
| 5,679,714 A | * | 10/1997 | Weg | 514/647 |
| 5,988,870 A | * | 11/1999 | Partsky | 366/348 |
| 5,989,582 A | * | 11/1999 | Weg | 424/434 |
| 6,271,240 B1 | * | 8/2001 | Simon | 514/282 |

FOREIGN PATENT DOCUMENTS

WO    WO 97/01337    *    1/1997

OTHER PUBLICATIONS

Swift, Robert, "Encyclopedia of Controlled Drug Delivery," Jul. 1999, vols. 1, 2, see http://www.wiley.co.uk/products/subject/reference/mathiowitz_sample_chapter.html.*

* cited by examiner

Primary Examiner—Brian L. Casler
Assistant Examiner—Jeremy Thissell
(74) Attorney, Agent, or Firm—Duane Morris LLP

(57) ABSTRACT

A drug dispensing system for substantially preventing addictive use of drugs. The system has multiple dispensers each containing a drug such as nasal spray. The drug in at least one of the dispensers is diluted to a first pre-selected concentration level with a diluent and the drug in at least a second one of the dispensers is diluted to a second lower pre-selected concentration level with a diluent.

17 Claims, 2 Drawing Sheets

DRUG DISPENSING SYSTEM

FIELD OF THE INVENTION

This invention relates to drug dispensing systems and in particular, to a nasal decongestant spray dispensing system that substantially prevents addiction from occurring when decongestant nasal sprays are used.

BACKGROUND OF THE INVENTION

Millions of people suffer from various symptoms of the common cold or other sinus-related problems, such as sinusitis and hay fever. Included among these symptoms is "rhinitis," a medical term for blocked or clogged sinuses. Symptomatic persons seeking relief from these symptoms typically use nasal decongestants which are available over-the-counter without a prescription. The most popular of these decongestants contain oxymetazoline or a pharmaceutically acceptable salt thereof. Other nasal preparations available over-the-counter contain compounds such as xylometazoline, naphazoline, phenylephrine and pharmaceutically acceptable salts thereof.

Nasal decongestants containing oxymetazoline, for example, offer fast and effective relief from nasal congestion. Unfortunately, oxymetazoline has undesired side-effects, one of which includes the likelihood of addiction if used beyond the recommended dosage period. Since many people who use nasal sprays remain symptomatic beyond the recommended dosage period, and despite warnings that the spray should not be used for more than three or four days, usage frequently continues beyond the dosage period. Thus, a person using the spray in an effort to seek relief from their continued symptoms will likely become addicted.

Addiction or habitual overuse of nasal spray has a long and documented history in medical literature. "Rhinitis Medicamentosa" used in identifying the addiction or habitual overuse is discussed in a 1994 article from the Department of Otorhinolaryngology at Söder Hospital, Karolinska Institute, Stockholm, Sweden, entitled "Overuse of Oxy- and Xylometazoline Nasal Sprays" by Peter Graf.

As described in the article, a compensatory vasodilation remains after the vasocontrictive effects of the drug have disappeared. The pathophysiology of this "rebound" swelling caused by use of nasal spray is not known. After repeated use, a person will find that their sinuses become clogged due to this "rebound" reaction to the spray. This leads a person to use the nasal spray repeatedly, causing increasing congestion. In time, the spray becomes increasingly less effective to the user. Alleviating this rebound swelling altogether requires that the use of the nasal spray be abruptly withdrawn, causing extreme discomfort due to severe nasal congestion.

One approach in treating this problem is immediate cessation, or stopping "cold turkey." This type of withdrawal is very difficult for people addicted to nasal sprays, as it causes extreme discomfort and in many cases, insomnia. Other approaches include prescribing topical steroid nasal inhalers or oral systemic steroids which have a multitude of undesired side effects. Relief from congestion can take days or weeks and sedatives are often needed to help people who are also suffering from insomnia as a result of the severe nasal congestion.

U.S. Pat. Nos. 4,970,240 and 5,114,979 describe an aqueous topical nasal decongestant containing oxymetazoline or a salt thereof to which a fruity flavor is added to mask the aftertaste of the composition. No provision is made for assisting the user in withdrawing from addiction to these compositions.

Methods and compositions for treating addiction to drugs, alcohol, and tobacco, such as those described in U.S. Pat. Nos. 5,272,149; 5,219,858; 5,198,230; 4,496,545; 3,885,027; 4,582,705; 4,500,515; 4,596,825; 5,656,255; 5,688,804; and 5,594,030 are of possible general interest.

An apparatus and method for diluting nasal sprays containing additive compounds are described in copending U.S. patent application Ser. No. 09/033,252 filed by Howard Paritsky on Mar. 2, 1998. The apparatus and method described therein aids people who are unable to stop using nasal sprays completely.

Accordingly, there is a need for a drug dispensing system which is effective, easy to use and substantially eliminates the likelihood of addiction to the addictive compounds such as are used in nasal sprays.

SUMMARY OF THE INVENTION

A drug dispensing system comprising multiple dispensers each containing a drug. The drug in at least one of the dispensers is diluted to a first pre-selected concentration level with a diluent. The drug can be a nasal decongestant spray.

Typically, the drug in at least a second one of the dispensers is diluted to a second pre-selected concentration level with a diluent, the second pre-selected concentration level being different from the first pre-selected concentration level.

In some embodiments of the system, the drug in the first one of the dispensers is not diluted with a diluent.

Further, a method which uses the above dispensing system to substantially prevent addictive use of a drug or help addicted person withdraw from the addictive use of the drug.

BRIEF DESCRIPTION OF THE DRAWINGS

The advantages, nature, and various additional features of the invention will appear more fully upon consideration of the illustrative embodiments now to be described in detail in connection with accompanying drawings wherein.

It should be understood that the drawings are for purposes of illustrating the concepts of the invention and are not to scale.

DETAILED DESCRIPTION OF THE INVENTION

Figure 1:
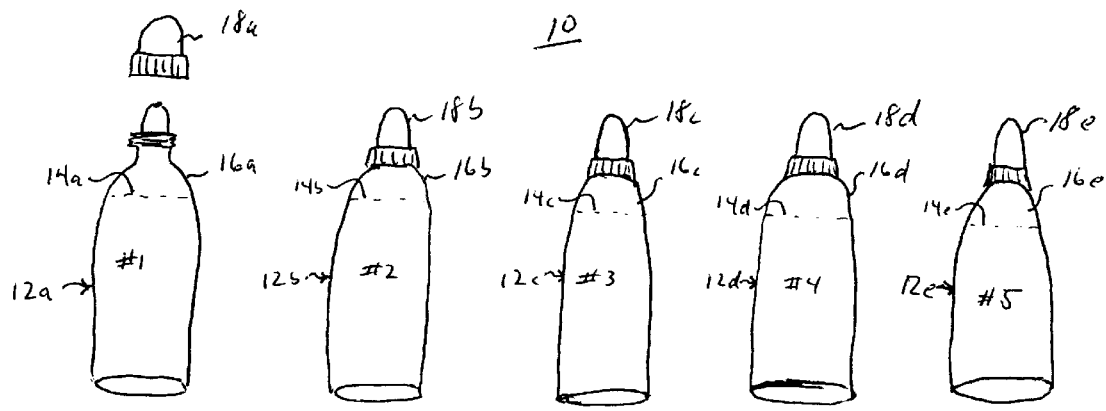
FIG. 1 is a schematic illustration depicting a drug dispensing system according to a first embodiment of the invention.

FIG. 1 shows a drug dispensing system 10 according to an embodiment of the present invention. The system 10 comprises a series of dispensers 12a–12e each containing a volume of solution 14a–14e having a pre-selected concentration of a drug such as nasal spray. The dispensers 12a–12e can be conventionally constructed and typically contain the same volume of solution. In the embodiment of the system depicted in FIG. 1, which is adapted for dispensing nasal spray, each dispensing dispenser 12a–12e comprises a standard plastic nasal solution squeeze bottle 16a–16e with a removable screw-type closure 18a–18e. Typically, the bottles will each contain about 5 to 10 ml. of solution.

The solution 14a contained in the first dispenser 12a of the series is composed of a 100% concentration (full strength) of conventionally formulated drug. In the shown embodiment, the nasal spray dispensed by the system can be an oxymetazoline-based formulation that includes 0.05% oxymetazoline hydrochloride or a pharmaceutically acceptable salt thereof, although other formulations known in the art can also be used such as xylometazoline, naphazoline, phenylephrine and pharmaceutically acceptable salts thereof.

The solutions 14b–14e contained in the remaining dispensers 12b–12e of the series are typically composed of the same formulation of the drug (i.e., nasal spray) as used in the first dispenser 14a. However, the strength or concentration of the drug in these solutions 14b–14e is successively reduced to a pre-selected level in each dispenser by the addition of a diluent such that the concentration of the drug in the solution 14e contained in the last dispenser 12e of the series is substantially reduced from that of the first dispenser 12a.

In the case of nasal spray, the diluent used in the solutions 14a–14e typically comprises a sodium chloride solution or distilled water. Preferably, the diluent comprises a 0.065% sodium chloride solution.

In the shown embodiment, the solution 14b in the second dispenser 12b is composed of 70 volume percent of nasal spray and 30 volume percent of diluent; the solution 14c in the third dispenser 12c is composed of 35 volume percent of nasal spray and 65 volume percent of diluent; the solution 14d in the fourth dispenser 12d is composed of 15 volume percent of nasal spray and 85 volume percent of diluent; and the solution 14e in the fifth dispenser 12e is composed of 5 volume percent of nasal spray and 95 volume percent of diluent.

The drug dispensing system 10 is used by selecting the first dispenser 12a in the series and using it conventionally to treat a corresponding medical condition for a predetermined time period. In the case of nasal spray, the first dispenser 12a is used as a conventional decongestant to treat nasal congestion. The solution 14a in the first dispenser 12a is used continuously to treat nasal congestion on the first day of the use of the system. Then the second dispenser 12b in the series is selected and used during the second day to treat nasal congestion. This use is repeated with each dispenser in the series until the solution 14e in the last dispenser 12e of the series has been used for one day. At this point, the desired decongestive effect will have been provided, but the rebound swelling of the sinuses will be eliminated or substantially reduced and no addiction to nasal spray will have occurred.

The rate at which the concentration of the drug (nasal spray) in each solution is decreased and the number of dispensers used in the system can all be tailored to the individual, depending on how often the individual uses the drug (nasal spray) and the amount used with each administration.

Figure 2:
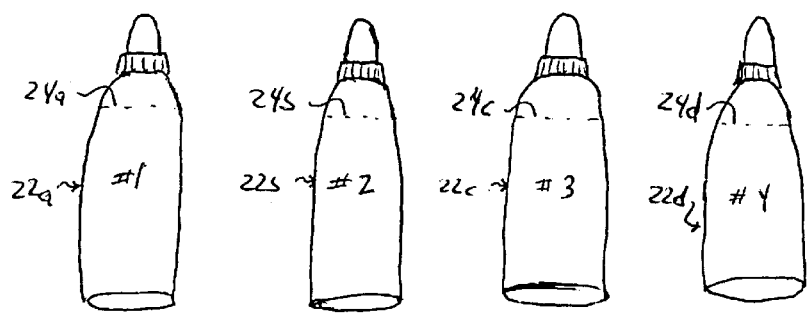
FIG. 2 is a schematic illustration depicting a drug dispensing system according to a second embodiment of the invention.
Figure 2:
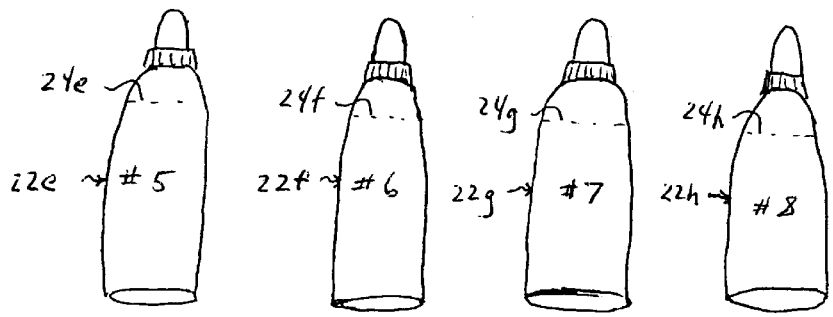

FIG. 2 shows a second embodiment of the system of the invention for treating nasal congestion. In this embodiment, the system 20 comprises 8 dispensers 22a–22h. The solution 24a in the first dispenser 22a is composed of 100 volume percent of nasal spray; the solution 24b in the second dispenser 22b is composed of 85 volume percent of nasal spray and 15 volume percent of diluent; the solution 24c in the third dispenser 22c is composed of 70 volume percent of nasal spray and 30 volume percent of diluent; the solution 24d in the fourth dispenser 22d is composed of 55 volume percent of nasal spray and 45 volume percent of diluent; the solution 24e in the fifth dispenser 22e is composed of 40 volume percent of nasal spray and 60 volume percent of diluent; the solution 24f in the sixth dispenser 22f is composed of 25 volume percent of nasal spray and 75 volume percent of diluent; the solution 24g in the seventh dispenser 22g is composed of 10 volume percent of nasal spray and 90 volume percent of diluent; and the solution 24h in the eighth dispenser 22h is composed of 5 volume percent of nasal spray and 95 volume percent of diluent.

In addition to preventing addictive use of a drug, the dispensing system of the invention as described by way of the examples above, can be also used for permitting a user to withdraw from addictive or habitual overuse of the drug. Moreover, in such uses, the system can be modified by diluting the starting concentration of drug in the solution of the first dispenser. These embodiments of the system will be especially useful in permitting gradual and comfortable withdrawal from the addictive compounds used in drugs such as nasal spray.

Figure 3:
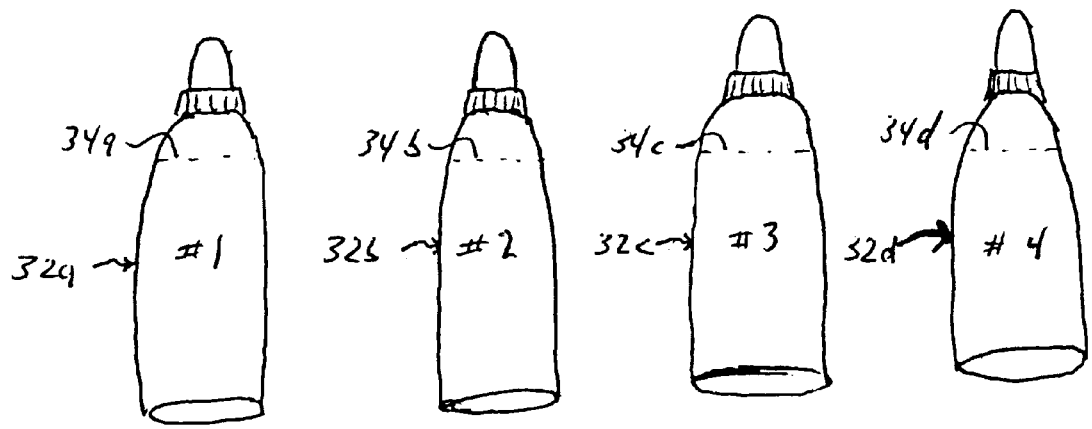
FIG. 3 is a schematic illustration depicting a drug dispensing system according to a third embodiment of the invention.
Figure 3:
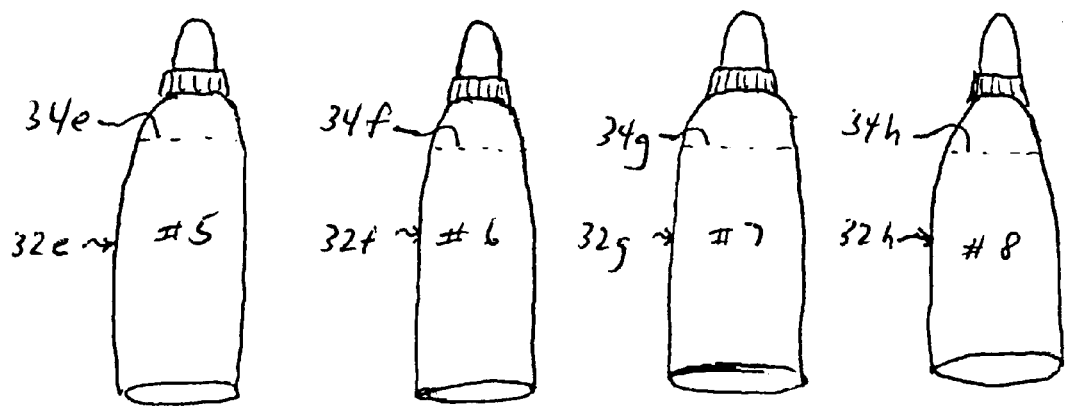

FIG. 3 shows a third embodiment of the system 30 of the invention which is especially useful for enabling a user to withdraw from addictive or habitual overuse of conventional nasal sprays. In this embodiment, the system comprises a series of dispensers 32a–32h as in the previous embodiments. However, the solution 34a in the first dispenser 32a is composed of 85 volume percent of nasal spray and 15 volume percent of diluent; the solution 34b in the second dispenser 32b is composed of 70 volume percent of nasal spray and 30 volume percent of diluent; the solution 34c in the third dispenser 32c is composed of 55 volume percent of nasal spray and 45 volume percent of diluent; the solution 34d in the fourth dispenser 32d is composed of 40 volume percent of nasal spray and 60 volume percent of diluent; the solution 34e in the fifth dispenser 32e is composed of 25 volume percent of nasal spray and 75 volume percent of diluent; the solution 34f in the sixth dispenser 32f is composed of 10 volume percent of nasal spray and 90 volume percent of diluent; the solution 34g in the seventh dispenser 32g is composed of 5 volume percent of nasal spray and 95 volume percent of diluent; and the solution 34h in the eighth dispenser 32h is composed of 1 volume percent of nasal spray and 99 volume percent of diluent.

As stated earlier, the dispensing system of the invention can also be applied to other types of drugs. For example, the system of the invention can also be used for dispensing topical nasal steroids.

While the foregoing invention has been described with reference to the above embodiments, various modifications and changes can be made without departing from the spirit of the invention. Accordingly, all such modifications and changes are considered to be within the scope of the appended claims.

What is claimed is:

1. A nasal spray dispensing system comprising:
   multiple dispensers each containing a nasal spray, the nasal spray being selected from the group of nasal decongestants and topical nasal steroids wherein the nasal spray in at least one of the dispensers being diluted to a first pre-selected concentration level with a diluent;
   wherein the nasal spray in at least a second one of the dispensers is diluted to a second pre-selected concentration level with a diluent, the second pre-selected concentration level being different from the first pre-selected concentration level.

2. The system according to claim 1, wherein a third one of the dispensers containing nasal spray is not diluted with a diluent.

3. The system according to claim 1, wherein the nasal spray in one of the dispensers is not diluted with a diluent.

4. The system according to claim 1, wherein the diluent is sodium chloride solution.

5. The system according to claim 1, wherein the diluent is distilled water.

6. The system according to claim 1, wherein the nasal spray includes an addictive compound.

7. The system according to claim 6, wherein the addictive compound is oxymetazoline.

8. The system according to claim 6, wherein the addictive compound is a pharmaceutically acceptable salt of oxymetazoline.

9. A method of preventing the addictive use of, or withdrawing from addictive use of a nasal spray, comprising the steps of:
providing a series of dispensers each containing a nasal spray, the nasal spray in at least some of the dispensers being diluted to pre-selected concentration levels with a diluent, the pre-selected concentration levels becoming progressively reduced in each successive dispenser;
using each dispenser to treat a medical condition for a predetermined period of time.

10. The method according to claim 9, wherein the medical condition is nasal congestion and the predetermined period of time is about one day.

11. The method according to claim 10, wherein the diluent is sodium chloride solution.

12. The method according to claim 10, wherein the diluent is distilled water.

13. The method according to claim 10, wherein the nasal spray includes an addictive compound.

14. The method according to claim 13, wherein the addictive compound is oxymetazoline.

15. The method according to claim 13, wherein the addictive compound is a pharmaceutically acceptable salt of oxymetazoline.

16. The method according to claim 10, wherein one of the dispensers contains nasal spray that is not diluted to a pre-selected concentration level with a diluent and further comprising the step of using the dispenser containing the undiluted nasal spray to treat nasal congestion prior to using the dispensers containing the progressively diluted nasal sprays.

17. The method according to claim 9, wherein the nasal spray in one of the dispensers is not diluted to a pre-selected concentration level with a diluent and further comprising the step of using the dispenser containing the undiluted nasal spray to treat the medical condition prior to using the dispensers containing the progressively diluted nasal sprays.

* * * * *